United States Patent [19]

Long, Jr.

[11] 4,073,879
[45] * Feb. 14, 1978

[54] BROMINATED PERFLUOROCARBON RADIOPAQUE AGENTS

[75] Inventor: David M. Long, Jr., El Cajon, Calif.

[73] Assignee: University of Illinois Foundation, Urbana, Ill.

[*] Notice: The portion of the term of this patent subsequent to Aug. 17, 1993, has been disclaimed.

[21] Appl. No.: 714,392

[22] Filed: Aug. 16, 1976

Related U.S. Application Data

[63] Continuation-in-part of Ser. No. 500,463, Aug. 26, 1974, Pat. No. 3,975,512, which is a continuation of Ser. No. 100,408, Dec. 21, 1970, abandoned.

[51] Int. Cl.$^2$ .............................................. A61K 29/02
[52] U.S. Cl. ...................................... 424/5; 252/312; 424/350; 424/352
[58] Field of Search ......................... 424/5, 350, 352; 252/312; 260/653, 648 F

[56] References Cited

U.S. PATENT DOCUMENTS

| | | | |
|---|---|---|---|
| 2,678,953 | 5/1954 | Conly | 260/653 |
| 3,055,953 | 9/1962 | Smeltz | 260/653.1 |
| 3,377,393 | 4/1968 | Yale | 260/653 |
| 3,381,042 | 4/1968 | Yale | 260/653 |
| 3,456,024 | 7/1969 | Loree | 260/653 |
| 3,499,089 | 3/1970 | Regan | 424/350 |
| 3,567,788 | 3/1971 | Carr et al. | 260/648 F |
| 3,574,774 | 4/1971 | Pews | 260/648 F |
| 3,975,512 | 8/1976 | Long | 424/5 |

*Primary Examiner*—Albert T. Meyers
*Assistant Examiner*—Vera C. Clarke
*Attorney, Agent, or Firm*—Merriam, Marshall & Bicknell

[57] ABSTRACT

Brominated cyclic and dibrominated aliphatic perfluorocarbons are useful as radiopaque agents for examination of the body of an animal.

13 Claims, No Drawings

BROMINATED PERFLUOROCARBON RADIOPAQUE AGENTS

This is a continuation-in-part of my copending application Ser. No. 500,463, filed Aug. 26, 1974, now U.S. Pat. No. 3,975,512, the disclosure of which is expressly incorporated by reference herein, which application is in turn a continuation of my application Ser. No. 100,408, filed Dec. 21, 1970, now abandoned.

The above identified applications and also my U.S. Pat. No. 3,818,229 disclose that certain brominated perfluorocarbons, including monobromo and dibromo aliphatic and cyclic perfluorocarbons, have radiopaque properties which render such compounds useful as radiopaque agents in radiologic examinations for detecting the presence of flaws or defects in, or otherwise examining the structure of, a wide variety of materials, including animals.

My U.S. Pat. No. 3,975,512 (application Ser. No. 500,463) covers the use of a preferred class of such compounds, specifically monobrominated acyclic perfluorocarbons, which have a desirably low level of toxicity, as radiopaque agents for medical applications.

The present invention relates to the use of brominated cyclic and dibrominated aliphatic perfluorocarbons as radiopaque agents for use in radiologic examination of the bodies of animals. Although the toxicity of the class of brominated perfluorocarbons with which this invention is concerned may, under certain circumstances, be greater than that of the monobrominated acyclic compounds, the toxic effects can be controlled, e.g., by limiting the amount of the dibrominated compounds to be used, so that practical use of the compounds of this invention is possible. The dibrominated and cyclic compounds, however, have in general a higher degree of radiopacity which gives them an advantage for use in certain applications, despite their higher degree of toxicity.

As employed herein, the term "radiopaque agent" means a substance which functions as a contrast media permitting X-ray visualization of one or more desired parts of a material, and the term "medical applications" refers to processes wherein one or more parts of the anatomy of an animal are contacted with a radiopaque agent.

In general, an ideal radiopaque agent for use in medical applications should be capable of producing clear concise shadows of the desired part or parts of the anatomy. It should also be shelf-stable, easily administered, and rapidly carried to the desired location(s) in the body for contrast. Moreover, it should be retained in the desired part or parts of the anatomy for a period of time necessary for the X-ray diagnosis or visualization and then excreted or eliminated rather rapidly without uncontrollable toxic effects.

In the prior art, barium sulfate has commonly been employed as a radiopaque agent for use in medical applications, particularly for roentgenologic examinations of the gastrointestinal tract in humans. In addition, soluble iodinated organic compounds, for example, sodium diatrizoate and meglumine diatrizoate, have also been used as radiopaque agents for urographic studies and the like. Certain fluoroiodo benzene compounds have been considered as radiopaque agents and found to be rather irritating to the gastrointestinal tract, making such compounds unacceptable for use in the gastrointestinal tract.

The radiopaque agents of the present invention include (1) monobrominated and dibrominated cyclic perfluorocarbons having 2 to 12 carbon atoms in the molecule, and (2) dibrominated acyclic perfluorocarbons having 5 to 12 carbon atoms in the molecule. A preferred group of compounds in both classes has about 6 to 8 carbon atoms in the molecule. The acyclic compounds can be straight or branched chain and the cyclic compounds can have one or two, preferably 5-carbon or 6-carbon, rings in the structure, as well as one or more alkyl side chains attached to the nucleus. In all cases, the location of the bromine substituent(s) is immaterial for purposes of the invention.

Bromofluorocarbons, including aliphatic monobromofluorocarbons, and their methods of manufacture are known and, per se, form no part of the present invention. Kirk-Othmer, *Encyclopedia of Chemical Technology*, Vol. 9, p. 748–750, Second Edition, describes, for example, the manufacture of aliphatic bromofluorocarbons.

The radiopaque agents of the present invention are liquid materials at ambient temperatures and are generally in the liquid state when used. For example, the radiopaque agent can be used as a pure liquid without any other materials or can also be used as a solution or an emulsion or suspension in which small particles of the radiopaque agent are dissolved, suspended or dispersed in a suitable vehicle or carrier, for example, Ringer's solution.

Such solutions or emulsions may also contain minor amounts of other ingredients, such as: buffers, e.g., sodium citrate; sequestering agents, e.g., disodium edetate; chemotherapeutic agents, e.g., nitrogen mustard; antibiotics, e.g., tetracycline; and/or one or more emulsifying agents, for example, "Pluronic F-68", a condensate of ethylene oxide with a hydrophobic base formed by condensing propylene oxide with propylene glycol.

In accordance with the invention, suitable aqueous emulsions contain the radiopaque agent in a concentration of about 1 to about 12 parts by volume for each part of the aqueous phase. The concentration, of course, affects the degree of radiodensity, as well as the viscosity of the radiopaque agent. When the concentration is less than about 0.5 part radiopaque agent per part by volume of aqueous phase, insufficient radiodensity results, and when the concentration exceeds about 12 parts the aqueous emulsion becomes viscous to the extent that problems of preparation and/or administration occur.

In addition to being employed in the liquid form, i.e., as either a pure liquid (i.e., about 99.98 to 100% active ingredient), a solution, or an emulsion, the radiopaque agents of the present invention can also be employed in the form of an aerosol. In this latter embodiment, the normally liquid radiopaque agent is confined in a container, under pressure, with one or more suitable aerosol propellents. Suitable propellents are well known in the aerosol formulation art and include, for example, fluorinated hydrocarbons, such as Propellents "11", "12", "114" and "313". One such aerosol formulation comprises about 20 wt.% $CF_3(CF_2)_6CF_2Br$, and about 80 wt.% of "Freon 12" (as the propellent).

The radiopaque agents of the present invention can be used or administered in medical applications according to procedure known in the art and used heretofore in administering prior art radiopaque agents. Thus, the radiopaque agents can be administered orally, rectally, intraperitoneally, subcutaneously, transtracheally, intravascularly, via catheters in the urinary bladder and ureters, intrathecally and via catheters in the bile ducts or pancreatic ducts, etc. The choice of a particular method of administration will depend, of course, upon the part or parts of the anatomy to be visualized, as well as upon the medical history and current medical status of the subject receiving the radiopaque agent.

The amount or dosage of radiopaque agent to be employed in any specific instance will, of course, be determined by those skilled in the art, and is not, per se, a part of the present invention. Generally, dosages on the order of about 1 to about 10 milliliters (of radiopaque agent) per kilogram (of body weight) (ml./kg,) are contemplated.

The present invention can be further understood by reference to the following illustrative example.

EXAMPLE I

Brominated perfluorocarbons of the present invention were administered to experimental animals. The identity and properties of the compounds used in these experiments are given in Table I. As is shown in the table, the radiopacity of the compounds ranged from 0.56 to 1.02. For comparison, Conray has a radiopacity of 0.80 on the same basis, while perfluoroctylbromide [$CF_3(CF_2)_6CF_2Br$] has a radiopacity value of 0.50.

TABLE I
PROPERTIES OF BROMINATED PERFLUOROCARBON COMPOUNDS

| Code Number | Formula | | Boiling Point (° C) | Density at 25° C (g/ml) | Relative Radiopacity* | Surface Tension (dynes/cm) |
|---|---|---|---|---|---|---|
| 2501 | $BR(CF_2)_4BR$ | | 97 | 2.100 | 0.81 | 19.6 |
| 2499 | $BRCF_2CF_2BR$ | | 47 | 2.165 | 1.02 | 19.7 |
| 2351 | (perfluorocyclohexyl-Br) | $C_6F_{11}BR$ | 90 | 1.970 | 0.56 | 18.3 |
| 2502 | (perfluorocyclohexyl-Br$_2$) | $C_6F_{10}BR_2$ | 138 | 2.195 | 0.71 | 22.3 |
| 2500 | $CF_3CFBRCF_2BR$ | | 72 | 2.156 | 1.02 | 19.6 |

*The radiopacity figure given is relative to Conray, with an arbitrary value of 0.80.

The compounds identified in Table I were orally administered to rats in amounts varying from 2 to 16 ml/kg. of body weight. In each case, the compound was passed into the lower esophagus or stomach by means of a flexible catheter and X-ray films were taken on a time schedule.

The radiographic density of each of the compounds was found to be satisfactory for outlining the gastrointestinal tract of the animals.

EXAMPLE II

Emulsions suitable for use in radiologic examination are prepared by adding two parts by volume of a brominated perfluorocarbon of the invention to 1 part by volume of lactated Ringer's solution containing a small amount (e.g., 6%) of an emulsifing agent, e.g., Pluronic F-68, and agitating in a roto-stator mixer until a stable emulsion is formed. More concentrated emulsions are formed by adding neat perfluorocarbon, up to a ratio of 12:1 by volume, and mixing until a stable emulsion is formed. Concentrated emulsions of this type, particularly those having perfluorocarbon/aqueous phase ratios of 6:1 to 10:1, are useful in medical applications requiring a high degree of radiopacity, as in examination of the tracheobronchial tree or in examination of the blood vessels of the kidney.

While the toxicity of the compounds of the invention appears to be greater than that of monobrominated acyclic fluorocarbons, the greater radiopacity permits smaller amounts of radiopaque to be used, thus overcoming the toxic effects. In addition, the higher radiopacity permits the compounds of the invention to be used in applications where the time available for X-ray exposure is limited, as in making X-ray motion pictures of the blood vessels of the kidney.

The foregoing detailed description has been given for clearness of understanding only, and no unnecessary limitations should be understood therefrom, as modifications will be obvious to those skilled in the art.

I claim:

1. In a process for radiologically examining a part of the body of an animal, the improvement comprising contacting said body part with an effective amount of a radiopaque agent comprising a dibrominated aliphatic perfluorocarbon or a brominated cyclic perfluorocarbon.

2. The process of claim 1 wherein said perfluorocarbon is selected from the class consisting of dibrominated acyclic perfluorocarbons, monobrominated cyclic perfluorocarbons, and dibrominated cyclic perfluorocarbons.

3. The process of claim 2 wherein said perfluorocarbon has 2 to 12 carbon atoms in its molecule.

4. The process of claim 3 wherein said perfluorocarbon has 6 to 8 carbon atoms in its molecule.

5. The process of claim 3 wherein said perfluorocarbon has the formula $BrCF_2-CF_2Br$.

6. The process of claim 3 wherein said perfluorocarbon has the formula $Br-(CF_2)_4-Br$.

7. The process of claim 3 wherein said perfluorocarbon has the formula

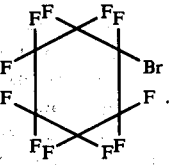

8. The process of claim 3 wherein said perfluorocarbon has the formula

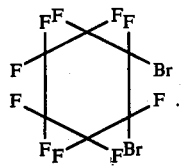

9. The process of claim 3 wherein said perfluorocarbon has the formula

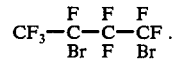

10. The process of claim 1 wherein said perfluorocarbon is administered in the form of an aqueous emulsion.

11. The process of claim 1 wherein said perfluorocarbon is administered in the form of an aerosol.

12. A non-toxic radiopaque emulsion consisting essentially of an aqueous phase, an effective amount of a dibrominated acyclic perfluorocarbon, a monobrominated cyclic perfluorocarbon, or a dibrominated cyclic perfluorocarbon, and a minor amount of an emulsifying agent.

13. An emulsion in accordance with claim 12 which contains about 1 to 12 parts by volume of said perfluorocarbon for each part by volume of aqueous phase.

* * * * *